United States Patent [19]

Enomoto et al.

[11] Patent Number: 5,071,753
[45] Date of Patent: Dec. 10, 1991

[54] PROCESS FOR THE ENZYMATIC PREPARATION OF ORGANIC ESTERS OF ASCORBIC ACID OR ERYTHORBIC ACID

[75] Inventors: Kanehiko Enomoto; Takao Miyamori; Akihiro Sakimae; Ryozo Numazawa, all of Otake, Japan

[73] Assignee: Mitsubishi Rayon Co., Ltd., Tokyo, Japan

[21] Appl. No.: 607,676

[22] Filed: Nov. 1, 1990

Related U.S. Application Data

[63] Continuation of Ser. No. 531,701, Jun. 1, 1990.

[30] Foreign Application Priority Data

Jun. 3, 1989 [JP] Japan ........................... 140252
Feb. 8, 1990 [JP] Japan ........................... 27069

[51] Int. Cl.$^5$ ................. C12P 17/04; C12P 7/40; C12N 9/18
[52] U.S. Cl. ................... 435/126; 435/134; 435/136; 435/137; 435/197
[58] Field of Search ............ 435/126, 134, 136, 137, 435/197, 280

[56] References Cited

U.S. PATENT DOCUMENTS 4,705,869 11/1987 Nickels et al. ............ 549/317
4,792,418 12/1988 Rubin et al. ............... 435/134
4,882,451 11/1989 Yoshida et al. .............. 435/280

OTHER PUBLICATIONS

Chem. Abs 75(30499k) (#5) (1971) Arakawa et al. Bitamin 1971 43(3,4) 166–71 (Japan).

*Primary Examiner*—Herbert J. Lilling
*Attorney, Agent, or Firm*—Oblon, Spivak, McClelland, Maier & Neustadt

[57] ABSTRACT

A process for the preparation of an organic ester of ascorbic acid or erythorbic acid represented by the general formula (II) or (III):

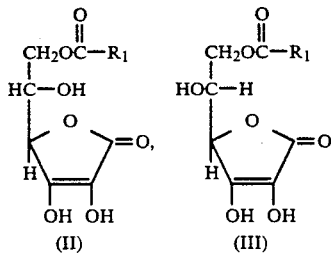

wherein $R_1$ is alkyl, aralkyl, or aryl, by reacting ascorbic acid or erythorbic acid with an organic or an ester thereof of the general formula (I):

wherein $R_1$ is as defined above and $R_2$ is hydrogen, methyl, ethyl or propyl, in an organic solvent in the presence of an ester hydrolase.

2 Claims, No Drawings

PROCESS FOR THE ENZYMATIC PREPARATION OF ORGANIC ESTERS OF ASCORBIC ACID OR ERYTHORBIC ACID

This is a continuation of application Ser. No. 531,701, filed on June 1, 1990.

INDUSTRIAL APPLICABILITY

The present invention relates to a process for the preparation of an organic acid ester of ascorbic acid or erythorbic acid by esterification or transesterification using an enzyme.

Ascorbic acid or erythorbic acid has been, because of its high reducing ability, widely used in foods, cosmetics, etc., as an antioxidant.

However, since these acids are only sparingly soluble in fat, they are converted into fat-soluble organic esters (e.g., palmitate, myristate, stearate, etc.) when used for prevention of the oxidation of fatty foods, for example, nuts, potato chips, mayonnaise, margarine, fried snack foods, and so on.

Some of the salts of the organic esters of ascorbic acid are useful as surface-active agent for foods and as discoloration-preventing agent for fruit, fresh flowers, etc.

PRIOR ART

Processes for the preparation of fatty acid esters of ascorbic acid/erythorbic acid have already been known. For example, the preparation of ascorbyl-6-palmitate is described in the Japanese Patent Appln. LOP Publn. No. 88,261/79, wherein hydrogen fluoride is used as a solvent and at the same time as a catalyst.

In addition, the Japanese Patent Appln. LOP Publn. No. 170,085/84 discloses a similar process wherein 96% sulfuric acid or higher is employed as a solvent and as a catalyst.

PROBLEMS TO BE SOLVED BY THE INVENTION

Hydrogen fluoride and sulfuric acid used in the prior art are strong acids and highly corrosive, and therefore this fact restricts the type of materials of the apparatus, making the procedure difficult. Under such circumstances, the present Inventors tried to eliminate the disadvantages of the prior art, and found that organic esters of ascorbic acid and erythorbic acid easily can be prepared from ascorbic acid or erythorbic acid and an organic acid or an ester thereof in an organic solvent utilizing the catalytic action of an ester hydrolase.

MEANS FOR SOLVING THE PROBLEM

The present invention relates to the following three processes (1) to (3).

(1) A process for the preparation of an organic ester of ascorbic acid or erythorbic acid represented by the general formula (II) or (III):

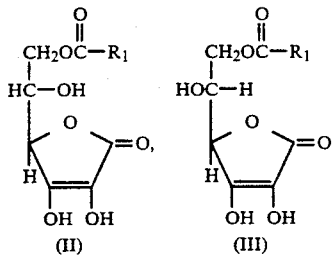

wherein $R_1$ is alkyl, aralkyl or aryl, which comprises reacting ascorbic acid or erythorbic acid with an organic acid or an ester thereof having the general formula (I):

$$R_1COOR_2 \qquad (I)$$

wherein $R_1$ is as defined above and $R_2$ is hydrogen, methyl, ethyl or propyl, in an organic solvent in the presence of an ester hydrolase.

(2) A process according to the above (1), wherein the reaction is carried out in the presence of 100 to 10,000 ppm of water.

(3) A process according to the above (1) or (2), wherein the ester hydrolase is immobilized on an insoluble carrier.

In the present process, the alkyl group $R_1$ in the above general formulas is not specifically defined, but includes not only lower alkyls such as methyl (the number of carbon atom=1), ethyl (the number of carbon atom=2), propyl (the number of carbon atom=3), etc., but also higher alkyls such as dodecyl (the number of carbon atoms=12), pentadecyl (the number of carbon atom=15), hexadecyl (the number of carbon atom=16), etc. Furthermore, unsaturated alkyls such as oleyl may also be included. As an example of aralkyl, benzyl may be mentioned, and phenyl may be exemplified as an aryl.

$R_2$ stands for hydrogen, methyl, ethyl or propyl, as defined above.

As mentioned above, the present compounds, organic esters of ascorbic acid or erythorbic acid, may be prepared utilizing biochemical ester synthesis in an organic solvent, by mixing ascorbic acid or erythorbic acid, an ester hydrolase and an organic acid and/or organic ester. In practice, the reaction rate is markedly improved when the reaction is carried out in the presence of 100 to 10,000 ppm, preferably 200 to 5,000 ppm of water.

The reaction according to the present invention should be carried out in solution or suspension. Since lower fatty acids such as propionic acid, butyric acid, or esters thereof remain in a liquid state at temperatures employed, they can also serve as a solvent. It is preferable, however, to employ organic solvents, such as methyl isobutyl ketone, ethyl ether, dioxane, etc., which dissolve ascorbic acid or erythorbic acid as well as fatty acids or esters thereof, for both cases of using higher organic acids or esters thereof and lower organic acids or esters thereof. The addition of water to the mixture to the amount of 100 to 10,000 ppm would be advantageous in the above cases.

Any ester hydrolase produced by animals, vegetables or microorganisms may be employed in the present invention if it possesses sufficient activity to effect esterification (or transesterification) of ascorbic acid or erythorbic acid with an organic acid or an ester thereof. Conventional preparations may be used regardless of the origin thereof, such examples include lipase, pancreatin, α-chymotrypsin, etc., and they are commercially available. Crude enzyme as well as purified one can be employed, and cells or disrupted cells containing the enzyme can also be employed as an enzyme source.

In addition, utilization of the enzyme (or enzyme source) immobilized on an insoluble carrier may bring about significant increase in yield.

Suitable insoluble carriers include inorganic carriers such as diatomite, porous glass, pumice, unglazed pottery and activated carbon; and organic carriers insoluble in a solvent employed, for example, polyethylene resin, polypropylene resin, ion exchange resin, cross-linked polyacrylamide resin. Among them, porous materials with large surface area are particularly preferred.

For immobilizing enzymes on the carriers, there are two methods, i.e. one method comprises immobilizing enzymes by ionic bond onto the surface of a carrier, and the other comprises immobilizing enzymes by covalent bond onto the surface of a carrier through aldehyde groups or isocyanate groups which have previously been introduced on the surface of the carrier. The enzyme is normally insoluble in an organic solvent, and since an immobilized enzyme seldom dissolves in the reaction solvent, an enzyme can easily, simply and stably immobilized by adding a carrier to an aqueous enzyme solution followed by mixing and drying.

Alternatively, the reaction may also be carried out by adding a predetermined amount of water to a mixture of an enzyme and/or immobilized enzyme, ascorbic acid or erythorbic acid and an organic acid or an ester thereof, and then stirring the resultant suspension. Further, the reaction may also be performed by applying a mixture of starting materials slowly onto a column in which an immobilized enzyme or microorganism has previously been packed. The reaction temperature ranges from 10° to 90° C., preferably 20° to 60° C. The separation of the product from the reaction mixture can be performed conventionally, for example, by extraction with an organic solvent followed by washing with water, and the like.

THE EFFECT OF THE INVENTION

When compared with conventional processes for the preparation of organic esters of ascorbic acid or erythorbic acid, the present invention provides a method which can be carried out in more mild conditions using apparatus of ordinary materials, and in which the purification of the product is very easy.

The present invention is further illustrated by the following Examples wherein all percentages are by weight unless otherwise stated.

EXAMPLE 1

3.0 g of ascorbic acid, 20.0 g of methyl stearate and 9.3 g of Lipase Amano "P" (Amano Pharmaceutical Co., Ltd. Nagoya, Japan) were suspended in 100 ml of dioxane and the mixture was allowed to react at 40° C. for 30 hours.

After the reaction was complete the suspension was filtered through a filter paper and the filtrate was evaporated to dryness under reduced pressure. The residue was washed three times with 100 ml of ether and the washings were combined and washed three times with 30 ml of a hemi-saturated NaCl solution, then dried over anhydrous sodium sulfate and filtered. After the solvent ether was removed with a rotary evaporator at 30° C., the residue was washed three times with 100 ml of hexane and dried in vacuo to give 0.6 g of a white solid. The solid showed a single peak on high-performance liquid chromatography. It was confirmed by NMR analyses that the solid is ascorbyl-6-stearate.

EXAMPLES 2 TO 10

5.68 mmol (1.0 g) of ascorbic acid and 1.0 g of Lipase Amano (Amano Pharmaceutical Co., Ltd.) were suspended in 100 ml of dioxane in a 300 ml-Erlenmeyer flask. To the suspension was added 5.68 mmol of fatty acid or ester thereof as indicated in Table 1, and the mixture was allowed to react at 40° C. for 48 hours with stirring.

After the reaction, the reaction mixture was filtered through 0.45 μm Millipore Filter (made of Teflon), and analyzed by high-performance liquid chromatography.

The yields of ascorbyl esters thus obtained are shown in Table 1.

TABLE 1

| Example No. | Fatty Acid or Fatty Acid Ester employed | Ascorbyl Ester (%) |
| --- | --- | --- |
| 2 | Isobutyric Acid | 0.133 |
| 3 | Methyl Isobutyrate | 0.151 |
| 4 | n-Caproic Acid | 0.220 |
| 5 | Methyl n-Caproate | 0.283 |
| 6 | Oleic Acid | 0.279 |
| 7 | Methyl Oleate | 0.281 |
| 8 | Palmitic Acid | 0.290 |
| 9 | Methyl Palmitate | 0.302 |
| 10 | Stearic Acid | 0.190 |

EXAMPLE 11

5.68 mmol (1.0 g) of erythorbic acid, 5.68 mmol (1.54 g) of methyl palmitate and 3 g of Lipase Amano M-10 (Amano Pharmaceutical Co., Ltd.) were suspended in 100 ml of methyl isobutyl ketone, and the mixture was allowed to react at 40° C. for 72 hours.

High-performance liquid chromatography of the mixture thus obtained showed that the concentration of erythorbyl palmitate was 0.180%.

EXAMPLES 12 TO 18

200 g of Molecular Sieves 4A 1/16 (Wako Jun-yaku Co., Ltd. Tokyo, Japan) was added to 2 l of dioxane and the mixture was allowed to stand for one day and filtrated in a dry box to obtain dehydrated dioxane. The water content of the dioxane thus obtained was determined by Karl-Fischer method and found to be less than 50 ppm.

To 100 ml aliquots of the dehydrated dioxane was added the indicated amount (ppm) each of distilled water as shown in Table 2. Then, 3 g of ascorbic acid, 20.0 g of methyl stearate, and 3 g of Lipase Amano "P" were added, and the mixture was allowed to react at 40° C. for 5 hours. Ascobyl stearate formed in the reaction mixture was analyzed by high-performance liquid chromatography, and the results obtained are shown in Table 2.

TABLE 2

| Example No. | The Amount of Distilled Water added (ppm) | Ascorbyl Stearate (%) |
| --- | --- | --- |
| 12 | 100 | 0.052 |
| 13 | 500 | 0.105 |
| 14 | 1,000 | 0.120 |
| 15 | 3,000 | 0.085 |

TABLE 2-continued

| Example No. | The Amount of Distilled Water added (ppm) | Ascorbyl Stearate (%) |
|---|---|---|
| 16 | 5,000 | 0.055 |
| 17 | 10,000 | 0.035 |
| 18 | 50,000 | 0.002 |
| Comparative Example | 0 | 0.024 |

EXAMPLE 19

5 g of Lipase Amano "P" (Amano Pharmaceutical Co., Ltd.) was dissolved in 500 ml of 1/20M phosphate buffer (pH 7.0), and 100 g of diatomite (Ishizu Pharmaceutical Co., Ltd. Osaka, Japan) was added thereto, followed by stirring at 30° C. for 1 hour.

The resultant mixture was transferred to a 2 liter round-bottom flask and was distilled under reduced pressure at 40° C., to give an immobilized enzyme powder.

1.0 g of ascorbic acid, 20.0 g of stearic acid and 100 ml of dioxane were charged into a 300 ml-Erlenmeyer flask, and allowed to dissolve with stirring at 40° C. Then, 20 g of the immobilized enzyme powder (containing 1.0 g of Lipase Amano "P") prepared as above was added and allowed to react at 40° C. for 24 hours.

The reaction mixture thus obtained was filtered through 0.45 μm Millipore Filter (made of Teflon ®) to remove the immobilized enzyme, and the resultant solution was subjected to high-performance liquid chromatography. The results showed that the concentration of ascorbyl stearate formed was 1.85%.

EXAMPLES 20 TO 24

0.5 g of Lipase Amano "P" (Amano Pharmaceutical Co., Ltd.) was dissolved in 50 ml of 1/20M phosphate buffer (pH 7.0), and 10 g each of insoluble carrier as indicated in Table 3 was added, stirred for 1 hour and distilled under reduced pressure at 40° C., to give various types of immobilized enzyme powders.

Then, 0.2 g ascorbic acid, 4.0 g of stearic acid and 20 ml of dioxane were placed in a 50 ml-Erlenmeyer flask, and allowed to dissolve with stirring at 40° C., followed by addition of 4.0 g of the immobilized enzyme obtained as above. The mixture was allowed to react at 40° C. for 24 hours.

The reaction mixture thus obtained was filtered through 0.45 μm Millipore Filter, and the concentration (%) of ascorbyl stearate formed was analyzed by high-performance liquid chromatography.

The relationship between the type of the immobilized enzyme (type of the carrier) and the amounts of ascorbyl stearate formed are shown in Table 3.

TABLE 3

| Example No. | Type of Immobilized Enzyme (Type of Carrier) | Ascorbyl Stearate (%) |
|---|---|---|
| 20 | Porous Silica Glass (CPG-10, Funakoshi Pharmaceutical Co., Ltd.) | 1.22 |
| 21 | Activated Carbon (Powder, Takeda Pharmaceutical Co., Ltd.) | 0.86 |
| 22 | Amberlite XAD-7 (Organo) | 0.91 |
| 23 | Porous Polypropylene Hollow Fiber (KPF 190C, Mitsubishi Rayon Co., Ltd.) | 1.03 |
| 24 | Porous Polyethylene Hollow Fiber (EHF 270G, Mitsubishi Rayon Co., Ltd.) | 1.19 |

EXAMPLES 25 TO 33

1.0 g of ascorbic acid and 10 g of immobilized enzyme powder (containing 0.5 g of Lipase Amano "P") prepared in the same manner as in Example 19 were suspended in 100 ml of dioxane in a 300 ml-Erlenmeyer flask. To the suspension was added 10 g each of the fatty acid or ester thereof as indicated in Table 4, and allowed to react at 40° C. for 48 hours with stirring, to give several types of fatty acid esters of ascorbic acid.

The reaction mixture thus obtained was filtered through 0.45 μm Millipore Filter (made by Teflon ®) and analyzed by high-performance liquid chromatography.

The amounts of the respective fatty acid esters of ascorbic acid are shown in Table 4.

TABLE 4

| Example No. | Fatty Acid or Fatty Acid Ester employed | Ascorbyl Ester (%) |
|---|---|---|
| 25 | Isobutyric Acid | 0.769 |
| 26 | Methyl Isobutyrate | 0.711 |
| 27 | n-Caproic Acid | 0.980 |
| 28 | Methyl n-Caproate | 0.889 |
| 29 | Oleic Acid | 1.21 |
| 30 | Methyl Oleate | 1.00 |
| 31 | Palmitic Acid | 1.81 |
| 32 | Methyl Palmitate | 1.55 |
| 33 | Methyl Stearate | 1.08 |

EXAMPLE 34

An immobilized enzyme powder was prepared in the same manner as in Example 19 except that Lipase Amano M-10 was used instead of Lipase Amano "P".

10 g of the immobilized enzyme powder (containing 0.5 g of Lipase Amano M-10), 1 g of erythorbic acid (5.68 mmol), and 10 g of palmitic acid were suspended in 100 ml of methyl isobutyl ketone, and allowed to react at 40° C. for 72 hours. The reaction mixture was filtered, and analyzed by high-performance liquid chromatography and found that the concentration of erythorbyl palmitate was 1.75%.

What is claimed is:

1. A process for the preparation of an organic ester of ascorbic acid or erythorbic acid represented by the general formula (II) or (III):

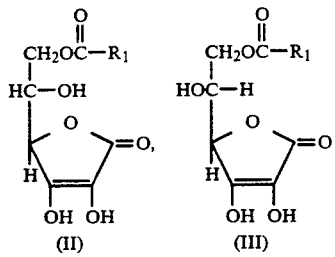

wherein $R_1$ is alkyl, which comprises reacting ascorbic acid or erythorbic acid with an organic acid or an ester thereof of the general formula (I):

$$R_1COOR_2 \qquad (I)$$

wherein $R_1$ is as defined above and $R_2$ is hydrogen, methyl, ethyl or propyl, in an organic solvent in the presence of a lipase; wherein said organic solvent dissolves ascorbic acid or erythorbic acid as well as fatty acids or esters thereof.

2. The process according to claim 1, wherein the lipase is immobilized on an insoluble carrier.

* * * * *